United States Patent

Regel et al.

Patent Number: 4,559,077
Date of Patent: Dec. 17, 1985

[54] AZOLYL-THIOETHER DERIVATIVES AS FUNGICIDES AND PLANT GROWTH REGULATORS

[75] Inventors: Erik Regel; Wilfried Draber, both of Wuppertal; Karl H. Büchel, Burscheid; Paul-Ernst Frohberger, Leverkusen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 454,303

[22] Filed: Dec. 29, 1982

[30] Foreign Application Priority Data

Jan. 9, 1982 [DE] Fed. Rep. of Germany ....... 3200414

[51] Int. Cl.⁴ .................... A01N 43/50; A01N 43/64; C07D 233/60; C07D 249/08
[52] U.S. Cl. .......................................... 71/76; 71/92; 514/184; 514/383; 514/399; 548/101; 548/262; 548/341
[58] Field of Search ........................ 548/101, 262, 341; 424/245, 269, 273 R; 71/76, 92; 514/184, 383, 399

[56] References Cited

U.S. PATENT DOCUMENTS

| 4,316,932 | 2/1982 | Kranz et al. | 548/101 |
| 4,331,674 | 5/1982 | Kramer et al. | 424/269 |
| 4,380,546 | 4/1983 | Sauter et al. | 548/341 |
| 4,382,944 | 5/1983 | Kramer et al. | 424/269 |

FOREIGN PATENT DOCUMENTS

| 0059894 | 9/1982 | European Pat. Off. | 548/269 |
| 2105490 | 8/1972 | Fed. Rep. of Germany | 548/341 |

*Primary Examiner*—Alton D. Rollins
*Attorney, Agent, or Firm*—Sprung, Horn, Kramer & Woods

[57] ABSTRACT

Compounds which are azolyl-thioether derivatives of the general formula

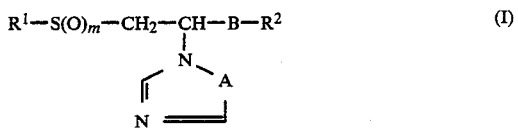

in which
A represents a nitrogen atom or a CH group,
B represents a CO or CH(OH) group,
m is 0 or 2,
$R^1$ represents an optionally substituted phenyl radical and
$R^2$ represents an optionally substituted cycloalkyl radical or a grouping of the general formula

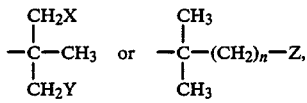

wherein
X and Y are identical or different and represent a hydrogen or halogen atom,
Z represents an alkyl, optionally substituted phenyl, optionally substituted phenoxy, optionally substituted phenylthio, optionally substituted benzyloxy, optionally substituted benzylthio, alkoxy, alkylthio, halogenoalkoxy, halogenoalkylthio, alkoxycar-onyl or cyano radical, and
n is 0 or 1, and the acid addition salts and metal salt complexes thereof, are novel and prepared by several processes described and find use as fungicides and as agents for regulating plant growth.

7 Claims, No Drawings

AZOLYL-THIOETHER DERIVATIVES AS FUNGICIDES AND PLANT GROWTH REGULATORS

The present invention relates to certain new azolyl-thioether derivatives, to several processes for their production, and to their use as fungicides and plant growth regulators.

It has already been disclosed that certain 1-halogeno-2,2-dimethyl-5-phenyl-4-triazolyl-pentan-3-ones, such as, for example, 2,2-dimethyl-1-fluoro-5-(4-methylphenyl)-4-(1,2,4-triazol-1-yl)-pentan-3-one, 2,2-dimethyl-1-fluoro-5-phenyl-4-(1,2,4-triazol-1-yl)-pentan-3-ol, 2,2-dimethyl-1-fluoro-5-(2,4-dichlorophenyl)-4-(1,2,4-triazol-1-yl)-pentan-3-one and 1-chloro-2,2-dimethyl-5-phenyl-4-(1,2,4-triazol-1-yl)-pentan-3-ol, possess good fungicidal and plant growth-regulating properties (see our DE-OS (German Published Specification) No. 2,951,164 and our DE-OS (German Published Specification) No. 2,951,163). However, the action of these compounds is not always completely satisfactory, in particular when low amounts and concentrations are used.

The present invention now provides as new compounds, the azolyl-thioether derivatives of the general formula

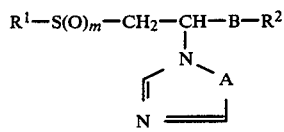

in which
A represents a nitrogen atom or a CH group,
B represents a CO or CH(OH) group,
m is 0 or 2,
$R^1$ represents an optionally substituted phenyl radical and
$R^2$ represents an optionally substituted cycloalkyl radical or a grouping of the general formula

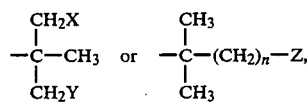

wherein
X and Y are identical or different and represent a hydrogen or halogen atom,
Z represents an alkyl, optionally substituted phenyl, optionally substituted phenoxy, optionally substituted phenylthio, optionally substituted benzyloxy, optionally substituted benzylthio, alkoxy, alkylthio, halogenoalkoxy, halogenoalkylthio, alkoxycarbonyl or cyano radical, and
n is 0 or 1,
and the acid addition salts and metal salt complexes thereof.

In the case in which B represents CH(OH), the compounds of the formula (I) possess two asymmetric carbon atoms; they can then be present in the erythro form as well as in the threo form. In general, they are obtained as diastereomer mixtures of varying composition. In all cases, they occur predominantly as racemates.

The invention also provides a process for the production of a compound of the present invention, characterized in that
(a) an azolyl-ketone of the general formula

in which
A and $R^2$ have the meanings given above, is reacted with formaldehyde or a formaldehyde-donating substance, such as paraformaldehyde, and a thio derivative of the general formula

in which
$R^1$ has the meaning given above, in the presence of a diluent and in the presence of a catalyst; and
(b), if a compound of formula (I) is required in which m is 2, the resulting compound of the general formula

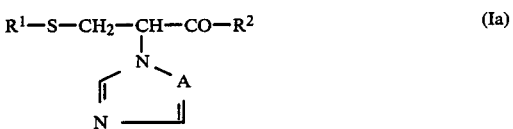

in which
A, $R^1$ and $R^2$ have the meanings given above, is oxidized to give the corresponding $SO_2$ derivative, and c), if a compound of formula (I) is required in which B represents a CH(OH) group, the compound obtained according to reaction variant (a) or (b) of the general formula

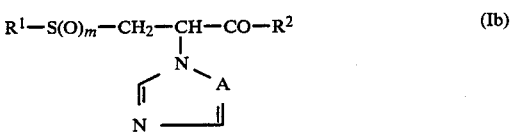

in which
A, $R^1$, $R^2$ and m have the meanings given above, is reduced to give the corresponding CH(OH) derivative; and if desired an acid or a metal salt is then added onto the compound of the formula (I) which has been obtained according to reaction variant (a), (b) or (c).

Finally, it has been found that the new azolyl-thioether derivatives of the formula (I) possess powerful fungicidal and plant growth-regulating properties. Surprisingly, the compounds according to the invention, of the formula (I), exhibit a better action in this respect than the compounds 2,2-dimethyl-1-fluoro-5-(4-methylphenyl)-4-(1,2,4-triazol-1-yl)-pentan-3-one, 2,2-dimethyl-1-fluoro-5-phenyl-4-(1,2,4-triazol-1-yl)-pentan-3-ol, 2,2-dimethyl-1-fluoro-5-(2,4-dichlorophenyl)-4-(1,2,4-triazol-1-yl)-pentan-3-one and 1-chloro-2,2-dimethyl-5-phenyl-4-(1,2,4-triazol-1-yl)-pentan-3-ol, which are known from the prior art and are similar compounds chemically and in respect of their action. The substances according to the invention thus represent an enrichment of the art.

Preferred compounds according to the present invention are those
in which
R¹ represents a phenyl radical which is optionally monosubstituted or polysubstituted by identical or different substituents (substituent(s) thereon preferably being selected from halogen; alkyl having 1 to 4 carbon atoms; halogenoalkyl, halogenoalkoxy and halogenoalkylthio, each having 1 or 2 carbon atoms and 1 to 5 identical or different halogen atoms, such as, especially, fluorine atoms and chlorine atoms; nitro; cyano; and phenyl which is optionally substituted by halogen and/or by alkyl having 1 or 2 carbon atoms);
R² represents a cycloalkyl radical which has 3 to 7 carbon atoms and is optionally substituted by alkyl having 1 to 4 carbon atoms, or represents a grouping of the general formula

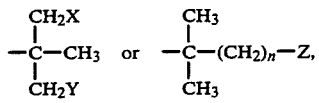

wherein
X and Y independently represent a hydrogen, fluorine or chlorine atom;
Z represents an alkyl radical having 1 to 4 carbon atoms, or represents a phenyl, phenoxy, phenylthio, benzyloxy or benzylthio radical, each of which is optionally substituted (preferred phenyl substituent(s) being selected from those preferred phenyl substituents which have already been mentioned in the case of R¹), or also represents an alkoxy or alkylthio radical, each having 1 to 4 carbon atoms, or a halogenoalkoxy or halogenoalkylthio radical, each having 1 or 2 carbon atoms and 1 to 5 identical or different halogen atoms (such as, especially, fluorine atoms and chlorine atoms), an alkoxycarbonyl radical having 1 to 4 carbon atoms in the alkyl part, or a cyano radical, and
A, B, m and n have the abovementioned meanings.

Particularly preferred compounds of the present invention are those,
in which
R¹ represents a phenyl radical which is optionally monosubstituted to trisubstituted by identical or different substituents selected from fluorine, chlorine, methyl, ethyl, isopropyl, tert.-butyl, trifluoromethyl, trifluoromethoxy, trifluoromethylthio, nitro, cyano, and phenyl which is optionally substituted by fluorine, chlorine and/or methyl;
R² represents a cyclopentyl, cyclohexyl or cyclopropyl radical which is optionally substituted by methyl, ethyl or propyl, or represents a grouping of the general formula

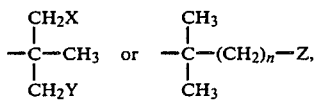

wherein
X and Y independently represent a hydrogen, fluorine or chlorine atom;
Z represents an alkyl, alkoxy or alkylthio radical, each having 1 to 4 carbon atoms, a trifluoromethoxy, trifluoromethylthio, methoxycarbonyl, ethoxycarbonyl, isopropoxycarbonyl, or cyano radical or a phenoxy, phenylthio, or phenyl radical which is optionally monosubstituted to trisubstituted by phenyl substituent(s) already mentioned immediately above as in the case of R¹; and
A, B, m and n have the abovementioned meanings.

Preferred compounds according to the invention, of course, also include addition products of acids on those azolyl-thioether derivatives of the formula (I) in which A, B, R¹ and R² and m have the respective meanings which have already been mentioned in respect of preferred and particularly preferred compounds in the invention.

The acids which may be used to form addition products include, as preference, hydrohalic acids (such as hydrobromic acid and, especially, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and naphthalene-1,5-disulphonic acid).

Preferred compounds according to the invention also include addition products of salts of metals of main group II to IV and sub-group I and II as well as IV to VIII with those azolyl-thioether derivatives of the formula (I) in which A, B, R¹ and R² and m have the respective meanings which have already been mentioned in the description of preferred and particularly preferred compounds of the invention.

In this context, salts of copper, zinc, manganese, magnesium, tin, iron and nickel are particularly preferred. Suitable anions of these salts are those which are derived from those acids which lead to physiologically tolerated addition products. Particularly preferred acids of this type in this connection are hydrohalic acids (such as hydrochloric acid and hydrobromic acid), and also phosphoric acid, nitric acid and sulphuric acid.

If, for example, 1,2,4-triazol-pinacolin, paraformaldehyde and 4-chlorothiophenol are used as starting materials, the course of the reaction variant (a) according to the invention can be represented by the following equation:

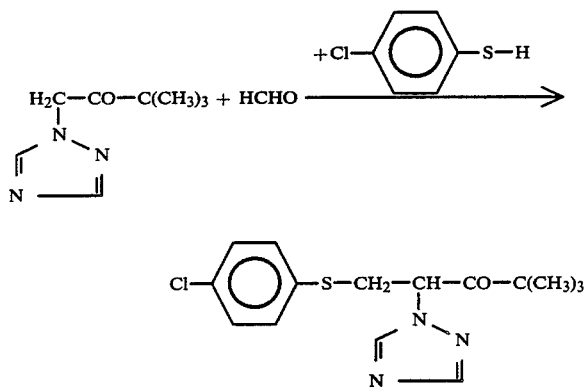

If, for example, 1-(4-chlorophenylthio)-4,4-dimethyl-2-(1,2,4-triazol-1-yl)-pentan-3-one and hydrogen peroxide in glacial acetic acid are used as starting materials, the course of the reaction variant (b) according to the invention can be represented by the following equation:

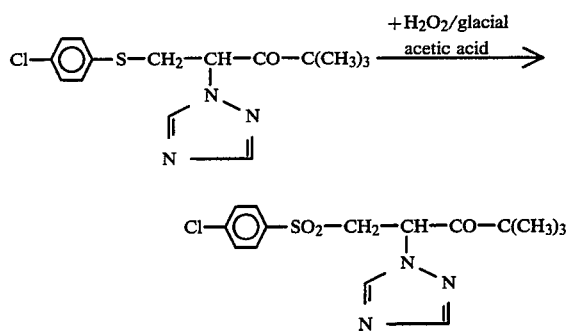

If, for example, 1-(4-chlorophenylthio)-4,4-dimethyl-2-(1,2,4-triazol-1-yl)-pentan-3-one and sodium borohydride are used as starting materials, the course of the reaction variant (c) according to the invention can be represented by the following equation:

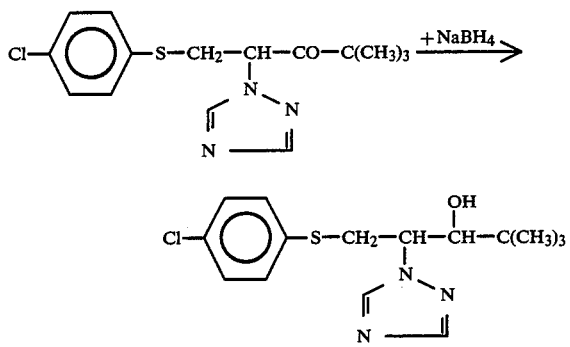

Preferred azolyl-ketones of formula (II) to be used as starting materials for reaction variant (a) according to the invention are those in which A and $R^2$ have those meanings which have already been mentioned for these substituents in connection with the description of the preferred and particularly preferred compound according to the invention.

The azolyl-ketones of the formula (II) are known, see U.S. Ser. No. 291,700 filed Aug. 19, 1981, now pending, DE-OS (German Published Specification) No. 2,638,470, U.S. Pat. No. 4,344,953 and DE-OS (German Published Specification) No. 3,010,560, or form the subject of, as yet unpublished, prior patent applications corresponding to German Patent Application No. P 3,028,330 of 7/25/80 (Le A 20 458) and U.S. Ser. No. 328,871 filed Dec. 8, 1981, now abandoned, and can be obtained in a generally known manner by reacting appropriate halogenoketones with 1,2,4-triazole or imidazole in the presence of an inert organic solvent (such as acetone), and in the presence of an acid-binding agent (such as potassium carbonate), preferably at the boiling point of the solvent used.

Preferred thio derivatives of formula (III) additionally to be used as starting materials for reaction variant (a) according to the invention are those in which $R^1$ has those meanings which have already been mentioned for this substituent in connection with the description of the preferred and particularly preferred compounds according to the invention.

The thio derivatives of the formula (III) are generally known compounds of organic chemistry.

Preferred diluents for reaction variant (a) according to the invention are organic solvents which are inert under the reaction conditions. These include, as preference, alcohols (such as methanol and ethanol), ethers (such as tetrahydrofuran and dioxane), aliphatic and cycloaliphatic hydrocarbons (such as hexane and cyclohexane), aromatic hydrocarbons (such as benzene, toluene and xylene) and halogenated aliphatic and aromatic hydrocarbons (such as methylene chloride and carbon tetrachloride, chloroform, chlorobenzene and dichlorobenzene).

Reaction variant (a) according to the invention is carried out in the presence of a catalyst. Any of the acidic and, especially, basic catalysts which can customarily be used, and buffer mixtures thereof, can be employed. These include, as preferences, Lewis acids, such as boron trifluoride, boron trichloride, tin tetrachloride or titanium tetrachloride; organic bases, such as pyridine and piperidine; and, especially, piperidine acetate.

In carrying out reaction variant (a) according to the invention, the reaction temperatures can be varied within a relatively wide range. In general, the reaction is carried out at a temperature between 20° and 160° C., preferably at the boiling point of the particular solvent.

In carrying out reaction variant (a) according to the invention, equimolar amounts are preferably employed, it being possible for the individual reactants to be present in excess or in less than the equimolar amount. The compounds of the formula (I) are isolated in a customary manner.

The oxidation of reaction variant (b) according to the invention is effected by reaction with the customary inorganic or organic oxidizing agents. These include, as preferences, organic per-acids (such as peracetic acid, p-nitroperbenzoic acid and m-chloroperbenzoic acid), inorganic per-acids (such as periodic acid), and furthermore hydrogen peroxide in glacial acetic acid or methanol, potassium permanganate and chromic acid.

In carrying out the oxidation, the reaction temperatures can be varied within a relatively wide range. In general, the reaction is carried out at a temperature between −50° and 100° C., preferably between 10° and 80° C.

In carrying out the oxidation according to the invention, about 1 to 5 mols of oxidizing agent (such as m-chloroperbenzoic acid in methylene chloride, or hydrogen peroxide in acetic anhydride or glacial acetic acid) are employed per mol of the compounds according to the invention, of the formula (Ia). The oxidation products are isolated in a customary manner. In a particular embodiment of the oxidation according to the invention, excess amounts of hydrogen peroxide in the presence of titanium-(III) chloride solution, at room temperature, are employed (in this context, also see Synthesis Communications, pages 205 et seq. (1981)). Surprisingly, the SO derivatives are not formed, as described in the stated publication, but the corresponding $SO_2$ derivatives.

The reduction of reaction variant (c) according to the invention is effected in a customary manner, such as, for example, by reaction with complex hydrides, if appropriate in the presence of a diluent, or by reaction with aluminum isopropylate in the presence of a diluent.

If the reaction is carried out with complex hydrides, suitable diluents for the reaction according to the invention are polar organic solvents. These include, as preferences, alcohols (such as methanol, ethanol, butanol and isopropanol) and ethers (such as diethyl ether or tetrahydrofuran). The reaction is carried out in general at a temperature between −15° C. and 30° C.; preferably between −15° and +20° C. For this purpose about 1 mol of a complex hydride (such as sodium borohydride, calcium borohydride or lithium alanate) is employed per mol of the ketone of the formula (Ib). To isolate the reduced compounds of the formula (I), the residue is taken up in dilute hydrochloric acid, and the solution is then rendered alkaline and extracted with an organic solvent. The further working-up is effected in a customary manner.

If the reaction is carried out with aluminum isopropylate, preferred diluents for the reaction according to the invention are alcohols (such as isopropanol) or inert hydrocarbons (such as benzene). The reaction temperatures can again be varied within a relatively wide range; in general the reaction is carried out at a temperature between 20° and 120° C., preferably at 50° to 100° C. To carry out the reaction, about 0.3 to 2 mols of aluminum isopropylate are employed per mol of the ketone of the formula (Ib). To isolate the reduced compounds of the formula (I), the excess solvent is removed in vacuo and the aluminum compounds formed are decomposed with dilute sulphuric acid or sodium hydroxide solution. The further working-up is effected in a customary manner.

The following acids are preferred for the preparation of physiologically tolerated acid addition salts of the compounds of the formula (I): hydrohalic acids (such as hydrobromic acid, and, especially hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid), and sulphonic acids (such as, for example, p-toluenesulphonic acid and naphthalene-1,5-disulphonic acid). The acid addition salts of the compounds of the formula (I) can be obtained in a simple manner by customary methods of salt formation, for example by dissolving a compound of the formula (I) in a suitable inert solvent and adding the acid (for example hydrochloric acid), and can be isolated in a known manner, for example by filtration, and if appropriate purified by washing with an inert organic solvent.

Salts of metals of main groups II to IV and of subgroups I to II and IV to VIII are preferred for the preparation of metal salt complexes of the compounds of the formula (I), copper, zinc, manganese, magnesium, tin, iron and nickel being mentioned as examples. Suitable anions of the salts are those which are preferably derived from the following acids: hydrohalic acids (such as hydrochloric acid and hydrobromic acid), and also phosphoric acid, nitric acid and sulphuric acid. The metal salt complexes of compounds of the formula (I) can be obtained in simple manner by customary processes, thus, for example, by dissolving the metal salt in alcohol (for example ethanol) and adding the solution to the compounds of the formula (I). Metal salt complexes can be isolated in a known manner, for example by filtration, and purified if appropriate by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating fungi which causes powdery mildew diseases, thus, for combating powdery mildew of barley (Erysiphe graminis); and for combating Phytophthora species, such as, against the late blight of tomato causative organism (Phytophthora infestans); and for combating rice diseases, such a Pyricularia oryzae and Pellicularia sasakii.

The active compounds according to the invention engate in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at borders, at airports or in fruit orchards. The inhibition of growth of herbaceous and woody plants at borders and in the vicinity of pipelines or overload lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stems of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya beans or cereals. Using growth regulators it is also possible, for example, to inhibit the degradation of desired constituents, such as sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plant, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled under the influence of growth regulators, so that defoliation of the plants at a desired point in time is achieved. Such defoliation is of great importance in the mechanical harvesting of cotton, but is also of interest for facilitating harvesting in other crops, such as in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

When used in appropriate amounts and concentrations, the substances according to the invention also exhibit a selective herbicidal action.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthlocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming or coating. Furthermore, it is possible to apply the active compounds in accordance with the ultra-low volume process or to inject the active compound preparation of the active compound itself into the soil. It is also possible to treat the seeds of plants.

When the compounds according to the invention are employed as plant growth regulators, the amounts applied can be varied within a relatively wide range. In general 0.01 to 50 kg, preferably 0.05 to 10 kg, are used per hectare of soil surface.

When the substances according to the invention are employed as fungicides, also, the amount applied can be varied within a relatively wide range, depending on the type of application.

Thus, expecially in the treatment of parts o plants, the active compound concentrations in the use forms are in general between 1 and 0.0001% by weight, preferably between 0.5 and 0.001% by weight.

In the treatment of seed, amounts of active compound of 0.001 to 50 g per kg of seed, preferably 0.01 to 10 g, are generally required.

In the treatment of soil, active compound concentrations of 0.00001 to 0.1% by weight, preferably of 0.0001 to 0.02%, are generally required at the place of action.

The present invention also provides plant growth regulating or fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

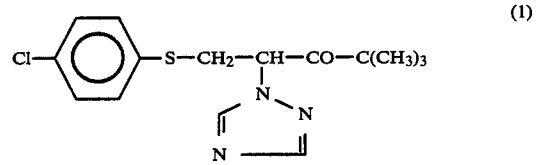

Reaction variant (a)

A mixture of 72.5 g (0.5 mol) of 4-chlorothiophenol, 100.2 g (0.6 mol) of 1,2,4-triazol-1-yl-pinacolin, 18 g (0.6 mol) of paraformaldehyde, 15 g of acetic acid and 5 ml of piperidine in 600 ml of toluene was heated under reflux in a water separator. After the water had been separated off, the reaction solution was washed with water, dried over sodium sulphate, filtered, and concentrated in vacuo. The oily residue was chromatographed over a silica gel column (mobile phase: chloroform). 45 g (28% of theory) of 1-(4-chlorophenylthio)-4,4-dimethyl-2-(1,2,4-triazol-1-yl)-pentan-3-one of melting point 67° C. were obtained.

Example 2

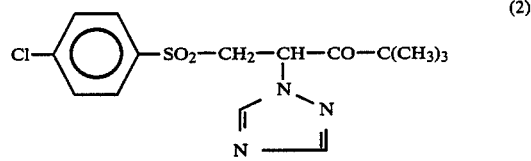

Reaction variant (b)

8.3 g (0.074 mol) of 30% strength hydrogen peroxide were slowly added dropwise to a solution of 22.6 g (0.07 mol) of 1-(4-chlorophenylthio)-4,4-dimethyl-2-(1,2,4-triazol-1-yl)-pentan-3-one (prepared as described in Example 1) in 100 ml of acetic acid and 2 drops of concentrated sulphuric acid. The reaction mixture was stirred for a further 18 hours at 60° C., and 8.3 g (0.074 mol) of 30% strength hydrogen peroxide were again added. The reaction mixture was then stirred for a further 18 hours at 80° C. Thereafter, the reaction solution was introduced into water, and the mixture was extracted with methylene chloride. The organic phase was dried over sodium sulphate, filtered, and concentrated in vacuo. The oily residue crystallized after being stirred with diisopropyl ether. 4.9 g (22% of theory) of 1-(4-chlorophenylsulphonyl)-4,4-dimethyl-2-(1,2,4-triazol-1-yl)-pentan-3-one of melting point 134° C. were obtained.

Example 3

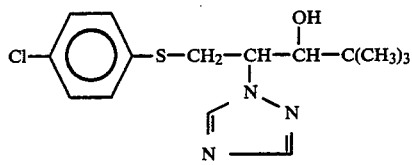 (3)

Reaction variant (c)

1.39 g (0.0367 mol) of sodium borohydride in 30 ml of water were slowly added dropwise to a mixture of 16.2 g (0.05 mol) of 1-(4-chlorophenylthio)-4,4-dimethyl-2-(1,2,4-triazol-1-yl)-pentan-3-one (prepared as described in Example 1) and 3.86 g (0.035 mol) of calcium chloride in 250 ml of isopropanol at −15° C. After 18 hours, the reaction mixture was concentrated in vacuo, the residue was taken up in methylene chloride, and the solution was washed with water, dried over sodium sulphate, filtered, and concentrated again. The oily residue crystallized after being triturated with diisopropyl ether. 14.3 g (87% of theory) of 1-(4-chlorophenylthio)-4,4-dimethyl-2-(1,2,4-triazol-1-yl)-pentan-3-ol of melting point 84° C. were obtained.

Example 4

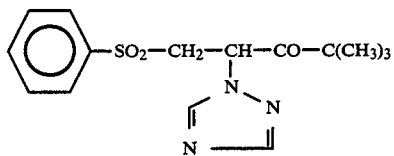 (4)

Reaction variant (b)

12.5 ml (0.121 mol) of 30% strength hydrogen peroxide were slowly added dropwise to a solution of 5 g (0.0173 mol) of 4,4-dimethyl-1-phenylthio-2-(1,2,4-triazol-1-yl)-pentan-3-one (obtained according to Example 1) and 14.83 ml (0.0346 mol) of 15% strength aqueous titanium(III) chloride solution in 20 ml of water and 100 ml of methanol at 25° C., while cooling. After 1 hour, the reaction mixture was extracted several times by shaking with chloroform. The combined organic phases were dried over sodium, sulphate, filtered and concentrated in vacuo. 5.2 g (98.5% of theory) of 4,4-dimethyl-1-phenylsulphonyl-2-(1,2,4-triazol-1-yl)-pentan-3-one of melting point 135° C. were obtained.

Example 5

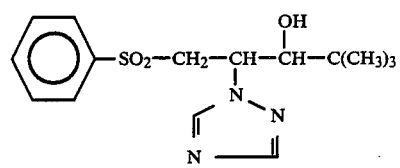 (5)

Reaction variant (c)

A solution of 0.87 g (0.0229 mol) of sodium borohydride in 20 ml of water was added dropwise to a suspension of 10 g (0.0328 mol) of 4,4-dimethyl-1-phenylsulphonyl-2-(1,2,4-triazol-1-yl)-pentan-3-one (obtained as described in Example 4) and 2.42 g (0.0221 mol) of calcium chloride in 150 ml of isopropanol at −10° C. After 18 hours, the reaction mixture was worked up according to Example 3. 7 g (68.6% of theory) of 4,4-dimethyl-1-phenylsulphonyl-2-(1,2,4-triazol-1-yl)-pentan-3-ol of melting point 145° C. were obtained.

The following compounds of the general formula (I) were obtained in a corresponding manner and according to the process variants (a), (b) and (c) according to the invention:

$$R^1-S(O)_m-CH_2-CH-B-R^2 \quad (I)$$

with N-A triazole ring on CH.

| Example No. | $R^1$ | m | A | B | $R^2$ | Meltingpoint (°C.) or $n_D^{20}$ |
|---|---|---|---|---|---|---|
| 6 | 2,4-Cl$_2$-C$_6$H$_3$ | 0 | N | CO | C(CH$_3$)$_3$ | 112 |
| 7 | 4-(CH$_3$)$_3$C-C$_6$H$_4$ | 0 | N | CO | C(CH$_3$)$_3$ | 54 |
| 8 | 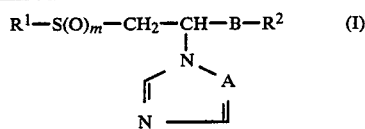 | 0 | N | CO | C(CH$_3$)$_3$ | viscous oil |

-continued
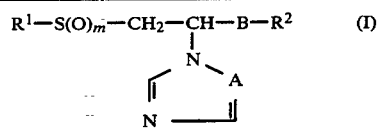
| Example No. | R¹ | m | A | B | R² | Melting point (°C.) or $n_D^{20}$ |
|---|---|---|---|---|---|---|
| 9 | 4-Cl-C₆H₄- | 0 | N | CO | —C(CH₃)₂CH₂Cl | 65 |
| 10 | 4-Cl-C₆H₄- | 0 | N | CO | —C(CH₂Cl)₂CH₃ | 72 |
| 11 | 4-Cl-C₆H₄- | 0 | N | CO | —C(CH₂F)₂CH₃ | 50 |
| 12 | 4-Cl-C₆H₄- | 2 | N | CO | —C(CH₃)₂CH₂F | 136 |
| 13 | 4-Cl-C₆H₄- | 2 | N | CO | —C(CH₃)₂CH₂Cl | 144 |
| 14 | 4-Cl-C₆H₄- | 2 | N | CO | —C(CH₂Cl)₂CH₃ | viscous oil |
| 15 | 2,4-Cl₂-C₆H₃- | 0 | N | CH(OH) | C(CH₃)₃ | 103 |
| 16 | 4-(CH₃)₃C-C₆H₄- | 0 | N | CH(OH) | C(CH₃)₃ | 106 |
| 17 | 4-Cl-C₆H₄- | 0 | N | CH(OH) | —C(CH₃)₂CH₂Cl | 103 |
| 18 | 4-Cl-C₆H₄- | 0 | N | CH(OH) | —C(CH₃)₂CH₂F | 89 |
| 19 | 4-(CH₃)₃C-C₆H₄- | 0 | N | CH(OH) | —C(CH₃)₂CH₂F | 90 |

-continued $$R^1-S(O)_m-CH_2-CH-B-R^2 \quad (I)$$

with N, A substituents forming a triazole/imidazole ring at the CH position.

| Example No. | $R^1$ | m | A | B | $R^2$ | Meltingpoint (°C.) or $n_D^{20}$ |
|---|---|---|---|---|---|---|
| 20 | 4-Cl-C$_6$H$_4$ | 0 | N | CH(OH) | —C(CH$_3$)$_2$CH$_2$OCH$_3$ | 68 |
| 21 | 4-Cl-C$_6$H$_4$ | 0 | N | CH(OH) | —C(CH$_3$)$_2$CO-OC$_2$H$_5$ | 70 |
| 22 | 4-Cl-C$_6$H$_4$ | 0 | N | CH(OH) | CH$_3$-cyclopropyl | 111 |
| 23 | 4-Cl-C$_6$H$_4$ | 2 | N | CH(OH) | C(CH$_3$)$_3$ | 175 |
| 24 | 4-Cl-C$_6$H$_4$ | 2 | N | CH(OH) | —C(CH$_3$)$_2$CH$_2$F | 158 |
| 25 | 4-Cl-C$_6$H$_4$ | 2 | N | CH(OH) | —C(CH$_3$)$_2$CH$_2$Cl | 204 |
| 26 | 4-Cl-C$_6$H$_4$ | 0 | CH | CO | C(CH$_3$)$_3$ | 1,5680 |
| 27 | 4-Cl-C$_6$H$_4$ | 0 | CH | CH(OH) | C(CH$_3$)$_3$ | 136 |
| 28 | 4-Cl-C$_6$H$_4$ | 2 | CH | CO | C(CH$_3$)$_3$ | 132 |
| 29 | C$_6$H$_5$ | 0 | N | CO | —C(CH$_2$F)$_2$CH$_3$ | 1,5479 |
| 30 | C$_6$H$_5$ | 0 | N | CO | —C(CH$_3$)$_2$CH$_2$Cl | 66 |
| 31 | C$_6$H$_5$ | 0 | N | CO | —C(CH$_3$)$_2$CH$_2$F | 1,5557 |

-continued $$R^1-S(O)_m-CH_2-\underset{\underset{N\underset{\phantom{N}}{\diagdown}}{\overset{N\diagdown}{\underset{\phantom{N}}{|}}}}{CH}-B-R^2 \quad (I)$$

| Example No. | R¹ | m | A | B | R² | Meltingpoint (°C.) or $n_D^{20}$ |
|---|---|---|---|---|---|---|
| 32 |  | 2 | N | CO | —C(CH₂F)₂CH₃ | 116 |
| 33 |  | 0 | N | CO | 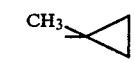 CH₃ | 1,5758 |
| 34 |  | 2 | N | CO | 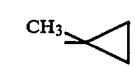 CH₃ | 108 |
| 35 |  | 2 | N | CO | —C(CH₃)₂CH₂Cl | 155 |
| 36 |  | 2 | N | CO | —C(CH₃)₂CH₂F | 134 |
| 37 | 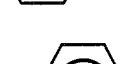 Cl— | 2 | CH | CH(OH) | —C(CH₃)₃ | 250 |

The plant growth regulating and fungicidal activity of the compounds of this invention is illustrated by the following biotest examples.

In these examples, the compounds according to the present invention are each identified by the number (given in brackets) of the corresponding preparative example.

The known comparison compounds are identified as follows:

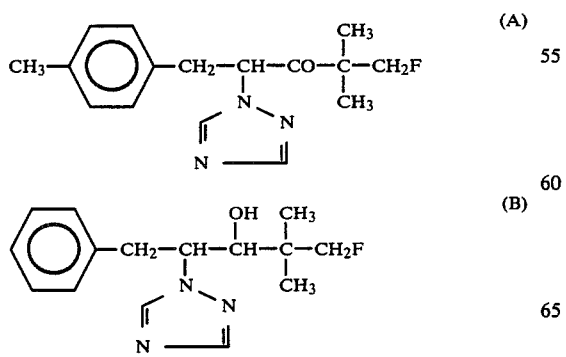

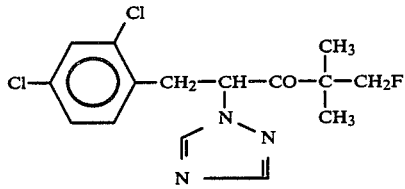

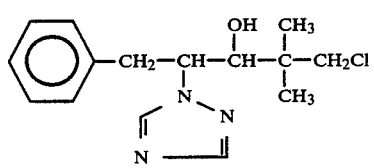

Example A

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f. sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art is shown, for example, by the compounds (6), (3), (17), (18), (21) and (12).

Example B

Influence on growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier, and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of the plants was measured and the influence on growth in per cent of the additional growth of the control plants was calculated. 0% influence on growth denoted a growth which corresponds to that of the control plants. Negative values characterized an inhibition of growth in comparison to the control plants, while positive values characterized a promotion of growth in comparison to the control plants.

In this test, the compounds (22), (3), (16), (15) and (7), for example, had a greater influence on growth than the compounds (B) and (C) known from the prior art.

Example C

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier, and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth of the plants was measured and the inhibition of growth in per cent of the additional growth of the control plants was calculated. 100% inhibition of growth meant that growth had stopped and 0% denoted a growth corresponding to that of the control plants.

In this test, compound (3), for example, showed a greater inhibition of growth than the compounds (A) and (C) known from the prior art.

Example D

Stimulation of the fixation of $CO_2$ in soy beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier, and the mixture was made up to the desired concentration with water.

Soya bean plants were grown in the greenhouse until the first secondary leaf had completely unfolded. At this stage, the plants were sprayed with the preparations of active compound until dripping wet. In the further course of the experiment, the fixation of $CO_2$ in the plants was determined by customary methods. The values were compared with those of the control plants, which had not been treated with the active compounds.

In this test, compounds (21) and (20), for example, showed a more powerful stimulation of the fixation of $CO_2$ than the compounds (A), (B) and (C) known from the prior art.

It is understood that the specification and examples are illustrative but not limitative of the present invention and that other embodiments within the spirit and scope of the invention will suggest themselves to those skilled in the art.

We claim:

1. An azolyl-thioether derivative of the formula

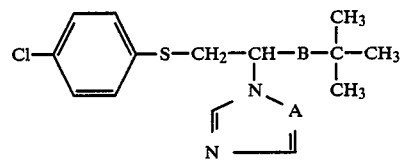

in which
A is a nitrogen atom or a CH group, and
B is a CO or CH(OH) group, or an addition product thereof with an acid or a metal salt.

2. A compound according to claim 1, wherein such compound is 1-(4-chlorophenylthio)-4,4-dimethyl-2-(1,2,4-triazol-1-yl)-pentan-3-one of the formula

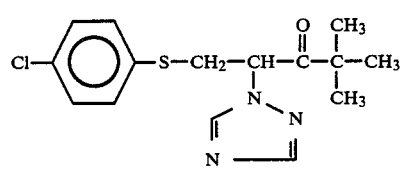

or an addition product thereof with an acid or a metal salt.

3. A compound according to claim 1, wherein such compound is 1-(4-chlorophenylthio)-4,4-dimethyl-2-(imidazol-1-yl)-pentan-3-ol of the formula

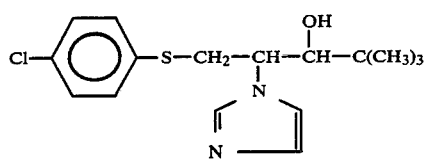

or an addition product thereof with an acid or a metal salt.

4. A fungicidal or plant growth regulating composition, comprising a fungicidally or plant growth-regulating effective amount of a compound or addition product according to claim 1.

5. A method of combating fungi comprising applying to the fungi, or to a habitat thereof, a fungicidally compound or addition product according to claim 1.

6. A method of regulating the growth of plants comprising applying to the plants, or a habitat thereof, a plant growth-regulating effective amount of a compound or addition product according to claim 1.

7. The method according to claim 5 or 6, wherein such compound is
1-(4-chlorophenylthio)-4,4-dimethyl-2-(1,2,4-triazol-1-yl)-pentan-3-one
1-(4-chlorophenylthio)-4,4-dimethyl-2-(imidazol-1-yl)-pentan-3-ol.

* * * * *